US00PP27902P3

(12) United States Plant Patent
Warner et al.

(10) Patent No.: US PP27,902 P3
(45) Date of Patent: Apr. 18, 2017

(54) ***STEVIA* PLANT NAMED '12-05-005'**

(50) Latin Name: *Stevia rebaudiana*
Varietal Denomination: 12-05-005

(71) Applicants: Board of Trustees of Michigan State University, East Lansing, MI (US); PureCircle Sdn Bhd, Negeri Sembilan (MY)

(72) Inventors: Ryan M. Warner, Lansing, MI (US); Randolph Beaudry, East Lansing, MI (US); James Hancock, East Lansing, MI (US); Veronica A. Vallejo, New Fairfield, CT (US)

(73) Assignees: Board of Trustees of Michigan State University, East Lansing, MI (US); PureCircle Sdn Bhd, Negeri Sembilan (MY)

( * ) Notice: Subject to any disclaimer, the term of this patent is extended or adjusted under 35 U.S.C. 154(b) by 129 days.

(21) Appl. No.: 14/544,192

(22) Filed: Dec. 8, 2014

(65) Prior Publication Data

US 2016/0165777 P1 Jun. 9, 2016

(51) Int. Cl.
*A01H 5/00* (2006.01)

(52) U.S. Cl.
USPC ..... Plt./258

(58) Field of Classification Search
USPC ..... Plt./263.1, 258
See application file for complete search history.

*Primary Examiner* — Keith Robinson
(74) *Attorney, Agent, or Firm* — McKee, Voorhees & Sease, PLC

(57) ABSTRACT

This invention relates to a new and distinct *stevia* plant designated as '12-05-005' primarily adapted to produce sweeteners.

1 Drawing Sheet

Genus and species: *Stevia rebaudiana.*
Variety denomination: '12-05-005'.

BACKGROUND AND SUMMARY OF THE INVENTION

I. Field & Utility Summary

This invention relates to a new and distinct *stevia* plant designated as '12-05-005' primarily adapted to produce sweetening agents. The new plant is characterized by a distinct steviol glycoside profile. *Stevia* variety '12-05-005' is a green herbaceous perennial which grows best in high light conditions, in well-drained soil.

II. Cultivation Summary

The new and distinct *stevia* plant '12-05-005' originated from bi-parental controlled cross of two selections from an open-pollinated population of *stevia* in East Lansing, Mich. Female parent '10-34' (unpatented) was crossed with male parent '10-19' (unpatented), in East Lansing, in 2012. *Stevia* '12-05-005' was selected from the plants resulting from the controlled cross of '10-34' and '10-19'.

III. Comparisons

*Stevia* '12-05-005' Characteristics

The following traits have been repeatedly observed and are determined to be unique characteristics of '12-05-005', which in combination distinguish this *stevia* plant as a new and distinct plant:

1. medium stevioside concentration
2. high rebaudioside A concentration
3. high rebaudioside C concentration
4. low rebaudioside D concentration
5. high rebaudioside M concentration
6. high total steviol glycosides concentration 7. high rebaudioside A percentage (w/w of total steviol glycosides)
8. low rebaudioside D percentage (w/w of total steviol glycosides)
9. medium rebaudioside M percentage (w/w of total steviol glycosides)

*Stevia* '12-05-005', parent '10-34', parent '10-19', comparator '12-05-144', and comparator '12-05-149' differ by the following combination of characteristics described in Table 1.

TABLE 1

| Genotype | Stevioside (mg/g) | Reb A (mg/g) | Reb C (mg/g) | Reb D (mg/g) | Reb M (mg/g) |
|---|---|---|---|---|---|
| 12-05-144 | 7.07 | 57.09 | 5.07 | 5.16 | 5.33 |
| 12-05-005 | 7.26 | 62.99 | 5.42 | 5.42 | 4.25 |
| 12-05-149 | 3.66 | 47.08 | 4.11 | 5.47 | 3.88 |
| 10-19 | 13.46 | 44.02 | 4.13 | 7.94 | 2.67 |
| 10-34 | 11.67 | 35.95 | 4.14 | 6.34 | 1.90 |

| Genotype | TSG (mg/g) | % Reb A | % Reb D | % Reb M |
|---|---|---|---|---|
| 12-05-144 | 79.72 | 71.6 | 6.47 | 6.69 |
| 12-05-005 | 85.34 | 73.8 | 6.35 | 4.98 |
| 12-05-149 | 64.20 | 73.3 | 8.52 | 6.04 |
| 10-19 | 72.23 | 60.9 | 11.00 | 3.70 |
| 10-34 | 60.01 | 59.9 | 10.56 | 3.17 |

Concentrations are in mg of compound per gram of dry leaf tissue;
TSG = total steviol glycosides Comparator Female Parent '10-34'

*Stevia* '12-05-005' is distinct from female parent '10-34' in that '12-05-005' has lower stevioside concentration, higher rebaudioside A concentration, higher rebaudioside C concentration, lower rebaudioside D concentration, higher rebaudioside M concentration, higher total steviol glycosides, higher rebaudioside A percentage (w/w of total steviol glycosides), lower rebaudioside D percentage (w/w of total steviol glycosides), and higher rebaudioside M percentage (w/w of total steviol glycosides) than female parent '10-34'.

Comparator Male Parent '10-19'

*Stevia* '12-05-005' is distinct from male parent '10-19' in that '12-05-005' has lower stevioside concentration, higher rebaudioside A concentration, higher rebaudioside C concentration, lower rebaudioside D concentration, higher rebaudioside M concentration, higher total steviol glycosides, higher rebaudioside A percentage (w/w of total steviol glycosides), lower rebaudioside D percentage (w/w of total steviol glycosides), and higher rebaudioside M percentage (w/w of total steviol glycosides) than male parent '10-19'.

Comparator '12-05-144'

*Stevia* '12-05-144' (co-pending application) is a selection from the same controlled cross of parent '10-34' and parent '10-19' from which '12-05-005' was selected.

*Stevia* '12-05-005' is distinct from comparator '12-05-144' in that '12-05-005' higher rebaudioside A concentration, lower rebaudioside M concentration, higher total steviol glycoside concentration, higher rebaudioside A percentage (w/w of total steviol glycosides), and lower rebaudioside M percentage (w/w of total steviol glycosides) than comparator '12-05-144'.

*Stevia* '12-05-005' is similar to comparator '12-05-144' in that '12-05-005' has similar stevioside concentration, similar rebaudioside C concentration, similar rebaudioside D concentration, and similar rebaudioside D percentage (w/w of total steviol glycosides) to comparator plant '12-05-144'.

Comparator '12-05-149'

*Stevia* '12-05-149' (co-pending application) is a selection from the same controlled cross of parent '10-34' and parent '10-19' from which '12-05-005' was selected.

*Stevia* '12-05-005' is distinct from comparator '12-05-149' in that '12-05-005' has higher stevioside concentration, higher rebaudioside A concentration, higher rebaudioside C concentration, higher rebaudioside M concentration, higher total steviol glycosides concentration, lower rebaudioside D percentage (w/w of total steviol glycosides), and lower rebaudioside M percentage (w/w of total steviol glycosides) than comparator '12-05-149'.

*Stevia* '12-05-005' is similar to comparator '12-05-149' in that '12-05-005' has similar rebaudioside D concentration and similar rebaudioside A percentage (w/w of total steviol glycosides) to comparator plant '12-05-149'.

IV. Breeding History

The new and distinct *stevia* originated from a controlled cross of the *stevia* selection '10-34' (female parent; unpatented)×*stevia* selection '10-19' (male parent; unpatented). This cross was made and the resulting seedlings grown in East Lansing, Mich. The present seedling was selected from the controlled breeding program in 2012 and was designated '12-05-005'.

V. Asexual Reproduction

*Stevia* plant '12-05-005' has been asexually propagated by cuttings since 2012 and was established in tissue culture in 2013 in East Lansing, Mich.

VI. Stability

Asexual propagation as described has demonstrated that the combination of traits that characterize this plant are fixed and remain true to type through at least five successive generations.

BRIEF DESCRIPTION OF THE FIGURES

The accompanying color photographs show typical specimens of the new plant at various stages of development as nearly true as it is possible to make in color reproductions. Color in the photographs may differ slightly from the color value cited in the detailed botanical description, which accurately describes the color of '12-05-005'. The photograph was taken in East Lansing, Mich. in October 2014.

FIG. 1 *Stevia* plant in field.

DETAILED DESCRIPTION OF THE INVENTION

The photographs together with the description of *stevia* '12-05-005' are based upon the observations taken during the 2014 growing season in East Lansing, Mich. The following description of *stevia* plant '12-05-005' contains references to color names taken from The Royal Horticultural Society Colour Chart (R.H.S.), 2001 edition. Botanical descriptions follow the Manual of Cultivated Plants (Bailey, 1949). *Stevia* plant '12-05-005' has not been observed under all possible environmental conditions and as such the characteristics may vary in detail depending on weather conditions, day length, soil type and location.

Plant (average, at maturity):

- *Shape.*—Upright to semi-upright.
- *Habit.*—Herbaceous perennial.
- *Branching habit.*—Freely branching basal nodes.
- *Number of nodes on main stem.*—19.
- *Height.*—370.5 mm.
- *Width.*—235.4 mm.
- *Number of stems arising from base.*—1.0.
- *Main stem length.*—370.5 mm.
- *Main stem diameter at midpoint.*—5.6.
- *Number of branches (arising from lower half of stem).*—6.0.
- *Branch angle from main stem.*—40°.
- *Main stem color.*—Green 141B.
- *Stem length.*—43 cm.
- *Stem diameter.*—9.5 mm.
- *Internode length.*—1.1 cm.
- *Stem texture.*—Pubescent.
- *Stem color.*—139D.

Leaves:

- *Shape.*—Simple.
- *Arrangement on stem.*—Generally opposite.
- *Margin.*—Serrated.
- *Dorsal color.*—Green 137B.
- *Ventral color.*—Green 137D.
- *Venation color.*—Green 137D.
- *Leaf angle from main stem.*—74°.
- *Width.*—10.7 mm.
- *Length, including petiole.*—44.9.
- *Thickness.*—<1 mm.
- *Length of petiole.*—2.7 mm.
- *Petiole color.*—Green 138B.
- *Petiole diameter.*—Blade attached directly to the stem.
- *Description of apex and base of leaf.*—Apex slightly serrated.

*Texture of leaf* (*upper and lower surfaces*).—Slightly pubescent.
*Leaf length.*—5.3 cm.
*Leaf width.*—1.1 cm.

Flowers:
*Type.*—Paniculate-corymbose.
*Floret shape.*—Tubular.
*Stigma.*—Exserted.
*Inflorescence diameter.*—5.0 mm.
*Depth of inflorescence.*—7.8 mm.
*Number of florets per inflorescence.*—4.8.
*Length of peduncle.*—13.5 mm.
*Number of sepals per floret.*—0.
*Number of petals per floret.*—1.
*Number of stigmas per floret.*—2.
*Floret diameter.*—4.2 mm.
*Bud color.*—Green 138B.
*Stigma color.*—White 155A.
*Petal color.*—White 155A.
*Sepal color.*—Green 138B.
*Basal buds.*—3.
*Blooming period.*—October to killing frost.
*Arrangement and fragrance of flower.*—Corymb; non-fragrant.

Fruit:
*Type.*—Achenes.

Disease resistance and climate tolerance: Resistant to aphids (family Aphididae), tolerant to wind.

What is claimed is:

1. A new and distinct *stevia* plant as herein described and illustrated.

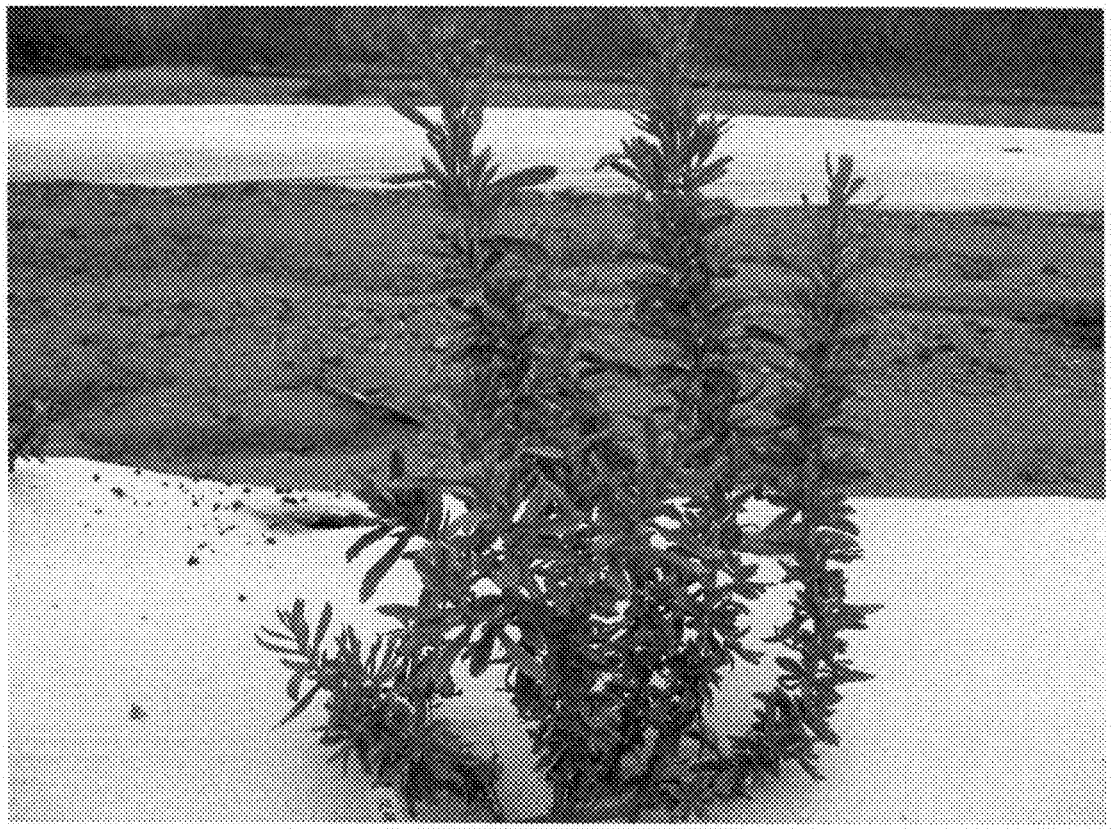

* * * * *